United States Patent [19]

Kuwana et al.

[11] Patent Number: 5,676,526
[45] Date of Patent: Oct. 14, 1997

[54] METHOD OF ELIMINATING BUBBLES IN A MEDICAL CENTRIFUGAL PUMP USING SPEED VARIATIONS

[75] Inventors: Katsuyuki Kuwana; Shuichi Ishii, both of Tokyo; Takeshi Aizawa, Haibara-gun; Kazuyuki Ito, Haibara-gun; Motonori Matsuura, Haibara-gun, all of Japan

[73] Assignee: Senko Medical Instrument Mfg. Co., Ltd., Tokyo, Japan

[21] Appl. No.: 392,966

[22] PCT Filed: Aug. 5, 1994

[86] PCT No.: PCT/JP94/01298

§ 371 Date: Jun. 1, 1995

§ 102(e) Date: Jun. 1, 1995

[87] PCT Pub. No.: WO95/04558

PCT Pub. Date: Feb. 16, 1995

[30] Foreign Application Priority Data

Aug. 6, 1993 [JP] Japan ................... 5-196541

[51] Int. Cl.$^6$ ................... F04B 17/03; F04B 15/00
[52] U.S. Cl. ................... 417/53; 417/423.1; 417/423.14; 415/1
[58] Field of Search ................... 417/53, 420, 423.1, 417/423.14; 415/1, 900

[56] References Cited

U.S. PATENT DOCUMENTS

| | | |
|---|---|---|
| 4,401,431 | 8/1983 | Arp ................... 604/4 |
| 4,643,641 | 2/1987 | Clausen et al. . |
| 5,084,244 | 1/1992 | Muramoto ................... 128/DIG. 3 |
| 5,316,440 | 5/1994 | Kijima et al. ................... 415/900 |
| 5,437,634 | 8/1995 | Amano ................... 604/65 |

FOREIGN PATENT DOCUMENTS

| | | |
|---|---|---|
| 0 543 172 | 5/1993 | European Pat. Off. . |
| 57-170746 U | 10/1982 | Japan . |
| A 6-121831 | 5/1994 | Japan . |

*Primary Examiner*—Roland McAndrews, Jr.
*Attorney, Agent, or Firm*—Fish & Richardson P.C.

[57] ABSTRACT

The present invention relates to a bubble elimination method in a medical centrifugal pump wherein a blood outlet 18 is directed upward so that a vertical line X passing through the enter point O of centrifugal pump main body 12 is positioned between two straight lines $\alpha, \beta$ which respectively pass through center point O and a point A and center point O and a point B, points A and B lying on the circumference of centrifugal chamber 15 where its periphery connects with blood outlet 18, and a blood inlet 17 is directed upward at an angle which is larger than the angle which is formed between the axis and the inner peripheral surface of centrifuge chamber 15, blood outlet 18 and blood inlet 17 being supported in these states by a drive portion 13 of the centrifugal pump main body 12. After filling the centrifuge chamber with blood and liquid filling, the processes of low speed drive, drive halt and high speed drive are sequentially carried out to rotating body 23. By means of this invention, it is possible to eliminate with surety the lingering of air bubbles inside centrifuge chamber 15 of centrifugal pump main body 12 when initiating circulation of the blood in the circulation path of an artificial heart-lung machine or the like.

9 Claims, 6 Drawing Sheets

METHOD OF ELIMINATING BUBBLES IN A MEDICAL CENTRIFUGAL PUMP USING SPEED VARIATIONS

TECHNICAL FIELD

The present invention relates to a method for eliminating air bubbles in a centrifugal pump which comprise an artificial heart-lung machine used to process liquid fluid which includes blood taken from a patient and then returning the processed blood and liquid fluid to the patient, during a procedure such as heart surgery.

BACKGROUND ART

In general, an artificial heart-lung machine which processes blood as it circulates the blood outside the body is designed to temporarily store in blood storage chamber 1 venous blood taken from a patient's vein via a blood drawing line, as shown in FIG. 3. In this design, the blood in this blood storage chamber 1 is relayed via a pump 2 to artificial lung 4 which has a heat exchanger 3. Blood which has undergone gas exchange at the artificial lung 4 is then returned to the patient's artery via a blood return line.

Roller pumps, which send out blood by squeezing the tube which forms the blood circulation path with a roller, and centrifugal pumps, which send out blood by means of centrifugal force, may be used as the pump 2 employed in this type of artificial heart-lung machine.

An explanation will now be made of the structure of the centrifugal pump using the figures. As shown in FIGS. 4 and 5, this centrifugal pump 11 is composed of a centrifugal pump main body 12 which sends out the blood which has been taken thereinto, and a driving portion 13 which drives this centrifugal pump main body 12.

Vessel 14 which forms centrifugal pump main body 12 has a centrifuge chamber 15, consisting of a conically shaped hollow portion, and a magnet chamber 16 which is sealed off from centrifuge chamber 15. A blood inlet 17 is formed to this vessel 14 lying along the axis thereof. Further, a blood outlet 18 is formed to the side of vessel 14 lying in the tangential direction of centrifuge chamber 15 at the side of vessel 14.

Further, a shaft 21 which is provided spanning between centrifuge chamber 15 and magnet chamber 16 is supported in a rotatable fashion inside vessel 14. A rotating body 23 which has a plurality of vanes 22,22 is affixed to the end of this shaft 21 which projects toward centrifugal chamber 15. Further, a circular magnet 24 is affixed to the end of shaft 21 which projects out toward the magnet chamber 16.

Further, drive portion 13, which is attached to centrifugal pump main body 12, supports centrifugal pump main body 12 in a state wherein its axis is horizontal and supports blood outlet 18 in a state wherein it is level above centrifugal pump main body 12 (see FIG. 5). A drive magnet 25 which is rotated by means of a motor (not shown) is provided to drive portion 13 in the vicinity of its attachment with centrifugal pump main body 12. By rotating this drive magnet 25 using the motor, magnet 24 of the centrifugal pump main body 12 can be rotated due to the magnet force from drive magnet 25.

When magnet 24 of centrifugal pump main body 12 is rotated by drive portion 13, rotating body 23 which has vanes 22,22 rotates. An eddy is generated in the blood within centrifuge chamber 15 by the vanes 22,22. The pressure on the outer periphery inside centrifuge chamber 15 becomes high, while the pressure in the vicinity blood inlet 17 becomes low.

In other words, a pressure difference is generated between the outer periphery of centrifuge chamber 15 and the vicinity of blood outlet 17. Blood is drawn from blood inlet 17, and blood in centrifuge chamber 15 is sent out from blood outlet 18.

Vessel 14 of the aforementioned centrifugal pump main body 12 is formed by assembling a funnel shaped body 31 (see FIG. 6) which forms centrifuge chamber 15 and a outlet portion 32 (see FIG. 7) which forms blood outlet 18.

The inner peripheral surface of centrifuge chamber 15 of the vessel 14 formed in the above described manner must be formed in a tapered shape which progressively widens in the direction moving away from blood inlet 17 so that funnel shaped body 31 can be withdrawn. For this reason, when circulation of the blood is initiated, as shown in FIG. 8, air bubbles sometimes linger at the site indicated by the letter D in the figures between the edge of the inner periphery of centrifuge chamber 15 and blood outlet 18.

Additionally, air bubbles also sometimes lingers at the site indicated by the letter K in FIG. 5 which is at a position on a portion of centrifuge chamber 15 which is higher than blood outlet 18.

In this case, as shown in FIG. 9, during manufacturing, the side portion of outlet portion. 32 may be made to coincide with the tangential line of funnel shaped body 31. However, in so doing, a sharp point must be formed at the area of contact between funnel shaped body 31 and outlet portion 32. This site is very weak, so that it can break or be damaged easily.

Further, when attempting to expel the air bubbles which linger at the aforementioned site by force by means of rotating rotating body 23 at high speed, the air bubbles are broken down into smaller air bubbles, becoming attached to the inner surface of the tube which forms the blood circulation path. Accordingly, to eliminate these attached air bubbles requires additional time and trouble.

Accordingly, the present invention was conceived out of consideration of the above described circumstances, and has as its objective the provision of a centrifugal pump and an air bubble elimination method which can eliminate air bubbles from lingering in the centrifuge chamber, and can eliminate remaining air bubbles which have become attached to the member elements of the centrifuge chamber.

DISCLOSURE OF THE INVENTION

The air bubble elimination method of the present invention is a method for application in a centrifugal pump comprising a drive portion and a centrifugal pump main body connected to the drive portion, the centrifugal pump main body being equipped with: a vessel wherein these is formed a blood inlet into which the liquid filling flows and a blood outlet from which the blood and liquid filling is sent out, the inner portion of this vessel forming the centrifuge chamber; a shaft which is rotated by the drive portion inside the vessel; a rotating body which is supported by the end of the shaft and rotates inside the centrifuge chamber of the vessel; and a plurality of vanes formed to the rotating body which employ centrifugal force on the blood and liquid filling taken in from the blood inlet by means of the rotation of the rotating body.

In this air bubble elimination method, a low speed drive process, a drive halt process and a high speed drive process are carried out sequentially. In the low speed drive process, which is intended to move the remaining air bubbles in the centrifuge chamber toward the blood inlet without breaking the air bubbles into smaller air bubbles, the pressure in the vicinity of the blood inlet is lowered by rotating the rotating body at low speed by means of the drive portion. In the drive halt process, which is intended to move the remaining air bubbles which have been moved toward the blood inlet, toward the blood outlet positioned above, the rotation of the rotating body is halted by the drive portion. In the high speed drive process, which is intended to expel from the blood outlet, the remaining air bubbles which have been moved toward the blood outlet the rotating body is rotated at high speed by the drive portion. As a result, when circulation of the blood is initiated, the remaining air bubbles attached to the inner wall or the like of the centrifugal pump main body can be eliminated easily and with surety, making it possible to greatly reduce the time and labor necessary for the air bubble elimination process at the time of initiation of the use of the centrifugal pump.

In the centrifugal pump main body, the blood inlet is formed along the axis of the shaft, and the blood outlet is formed at the upper portion of the vessel to the side thereof along the tangential direction. The blood outlet is directed upward, supported in this state by the drive portion so that the vertical line passing through the center point of the centrifugal pump main body is positioned between two straight lines which respectively link the aforementioned center point and two connection points in the circumferential direction at the site of connection between the blood outlet and the centrifuge chamber. As a result, the air bubbles in the centrifuge chamber are eliminated naturally as a result of buoyant force.

Further, the inner peripheral surface of the centrifuge chamber in this centrifugal pump main body is tapered so as to widen in the direction moving away from the blood outlet. The blood inlet is directed upward, supported in this state by the drive portion, at an angle that is larger than the angle formed between the inner peripheral surface of the centrifuge chamber and the axis. As a result, the air bubbles in the centrifuge chamber are eliminated naturally by means of buoyant force.

In the low speed drive process, the rotating body of the centrifugal pump main body is rotated at 500 to 1500 rpm. As a result, the remaining air bubbles can be moved toward the blood inlet without being broken down into smaller air bubbles.

Moreover, the duration of the rotation of the rotating body of the centrifugal pump main body in the low speed drive process is 5 to 30 seconds. As a result, the remaining air bubbles can be moved toward the blood inlet with surety.

Further, the duration during which the rotating body of the centrifugal pump main body is halted in the drive halt process is 5 to 30 seconds. As a result, the air bubbles which have accumulated in the vicinity of the blood inlet can be moved toward the upper end of the centrifuge chamber with surety.

Furthermore, the rotating body of the centrifugal pump main body is rotated at 2500 to 5000 rpm during the high speed drive process. As a result, the air bubbles which have been moved to the vicinity of the upper end of the centrifugal chamber can be flushed out from the blood outlet due to centrifugal force.

Moreover, the duration of the rotation of the rotating body of the centrifugal pump main body in the high speed drive process is 10 to 120 seconds. As a result, air bubbles can be flushed out from the blood outlet with surety.

A magnetic body is provided to the shaft in the centrifugal pump main body. The drive portion has a drive magnet which rotates by means of a motor. By rotating the drive magnet using the motor, the magnetic body is attracted to the drive magnet and is rotated. As a result, the rotating body can be rotated in a non-contact state.

Moreover, the centrifugal pump of the present invention is comprised of a drive portion and a centrifugal pump main body which is attached to the drive portion. In a centrifugal pump which circulates blood and liquid filling through a path in an artificial heart-lung machine or the like, the centrifugal pump main body is provided with: a vessel wherein there is formed a blood take-in container into which the blood and liquid filling flows and a blood outlet from which the blood and liquid filling is sent out, the inner portion of this vessel forming the centrifuge chamber; a shaft which is rotated by the drive portion inside the vessel; a rotating body which is supported by the end of the shaft and rotates inside the centrifuge chamber of the vessel; and a plurality of vanes which form the rotating body and employ centrifugal force upon the blood and liquid filling taken in from the blood inlet by rotating the rotating body.

In the centrifugal pump main body, the blood inlet is formed along the axis of the shaft, and blood outlet is formed at the upper portion of the vessel to the side thereof along the tangential direction. The drive portion is supported in a state wherein the blood outlet is directed upward so that a vertical line passing through the center point of the centrifugal pump main body is positioned between two straight lines linking the aforementioned center point and a connection point between two points on the circumference at the connection site between the blood outlet and the centrifuge chamber. As a result, the air bubbles in the centrifuge chamber are eliminated naturally as a result of buoyant force.

Further, the inner peripheral surface of the centrifuge chamber in this centrifugal pump main body is tapered so as to widen in the direction moving away from the blood inlet. The blood take-in container is directed upward, supported in this state by the drive portion at an angle which is larger than the angle formed between the inner peripheral surface of the centrifuge chamber and the axis. As a result, the air bubbles in the centrifuge chamber are eliminated naturally due to buoyant force.

Further, a magnetic body is provided to the shaft in the centrifugal pump main body. The drive portion has a drive magnet which is rotated by means of a motor. By rotating the drive magnet using the motor, the magnetic body is attracted to the drive magnet and is rotated. As a result, the rotating body can be rotated in a non-contact state.

A BRIEF DESCRIPTION OF THE FIGURES

PREFERRED EMBODIMENTS OF THE PRESENT INVENTION

Preferred embodiments of the bubble elimination method in a medical centrifugal pump according to the present invention will be explained below with reference to the figures.

Additionally, it is noted here that where structural parts are identical to those in the centrifugal pump described above, the same numeric symbol will be employed and an explanation will be omitted.

Figure 1:
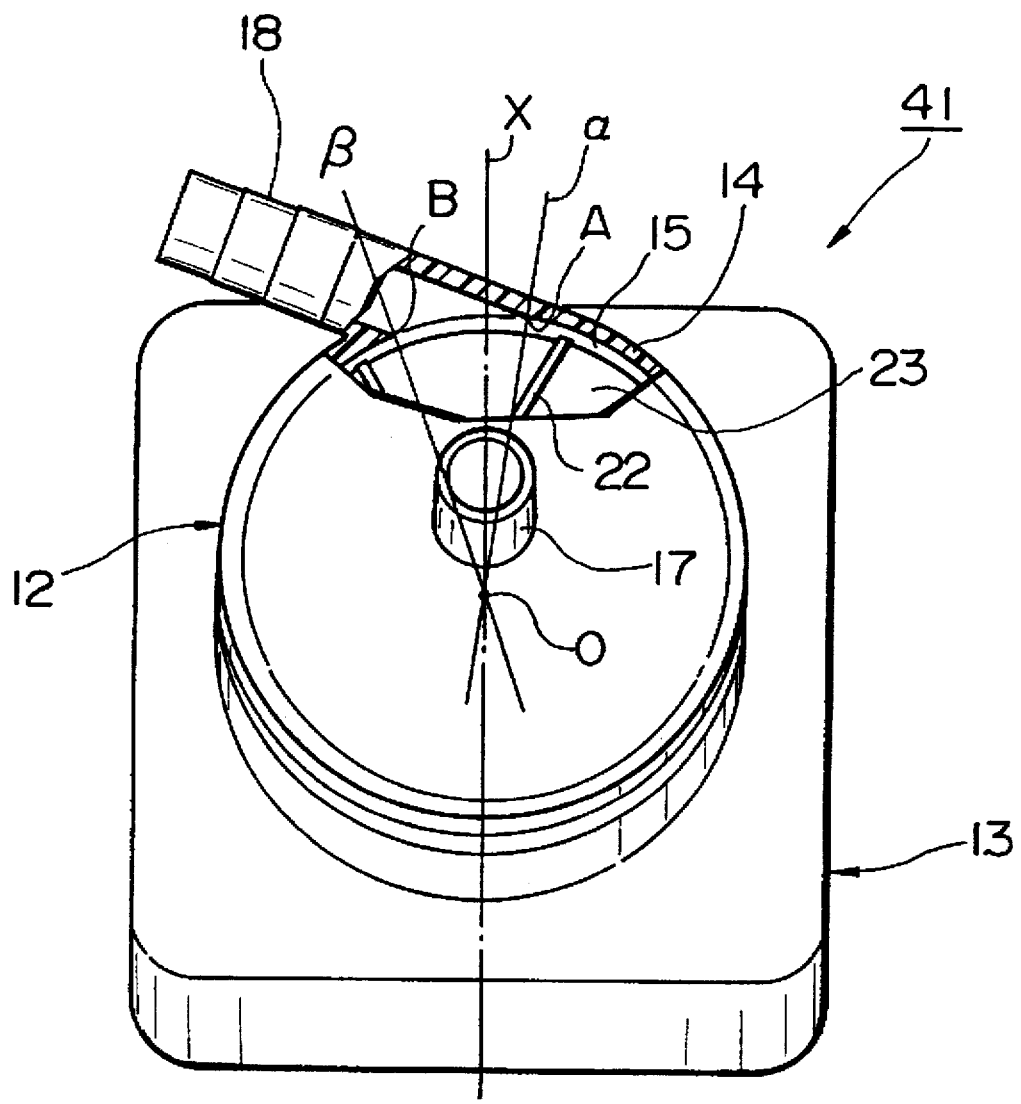
FIG. 1 is a front view of a centrifugal pump provided to explain the centrifugal pump in the embodiment of the present invention.
Figure 2:
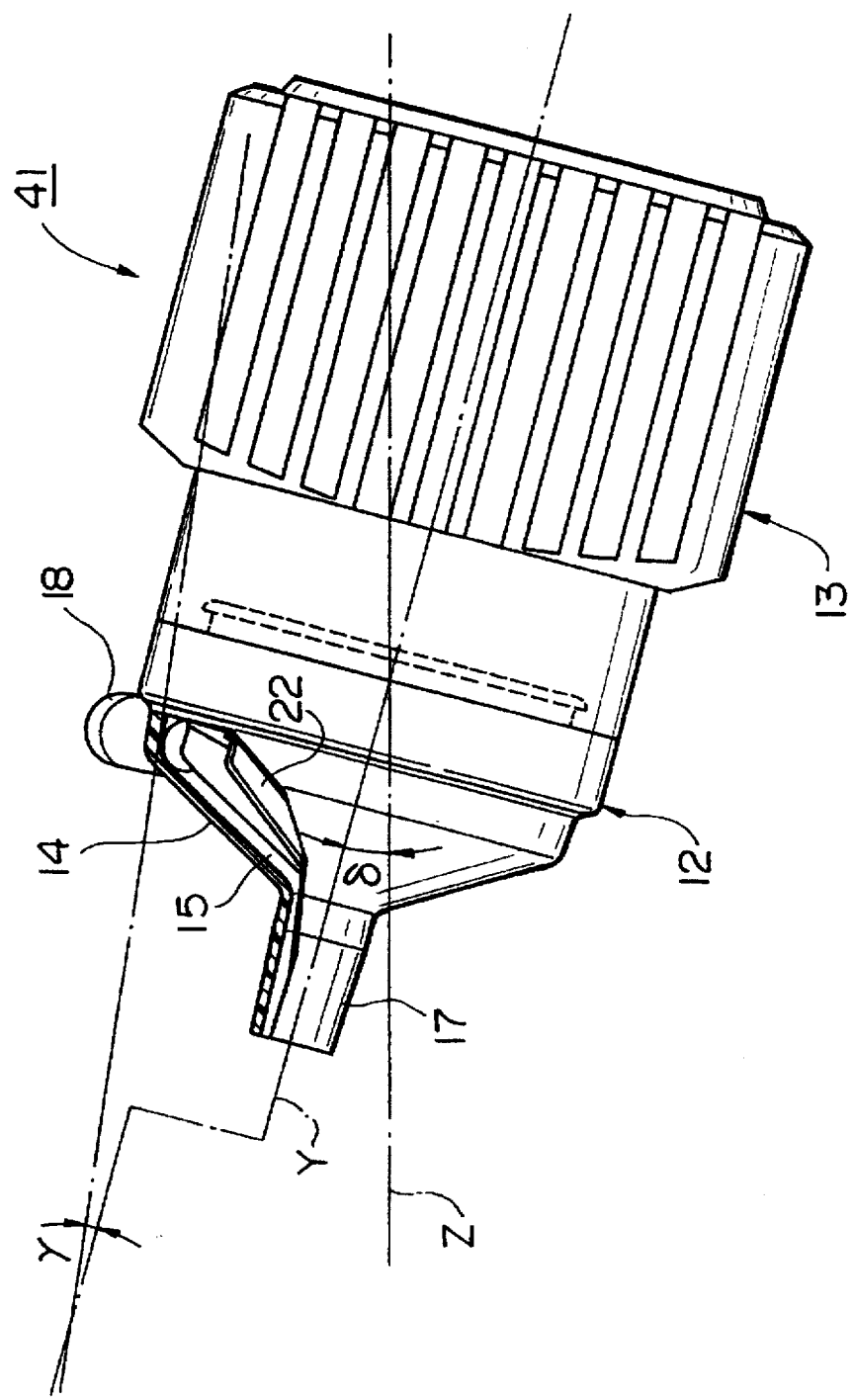
FIG. 2 is a side view of a centrifugal pump provided to explain the centrifugal pump in the embodiment of the present invention.
Figure 3:
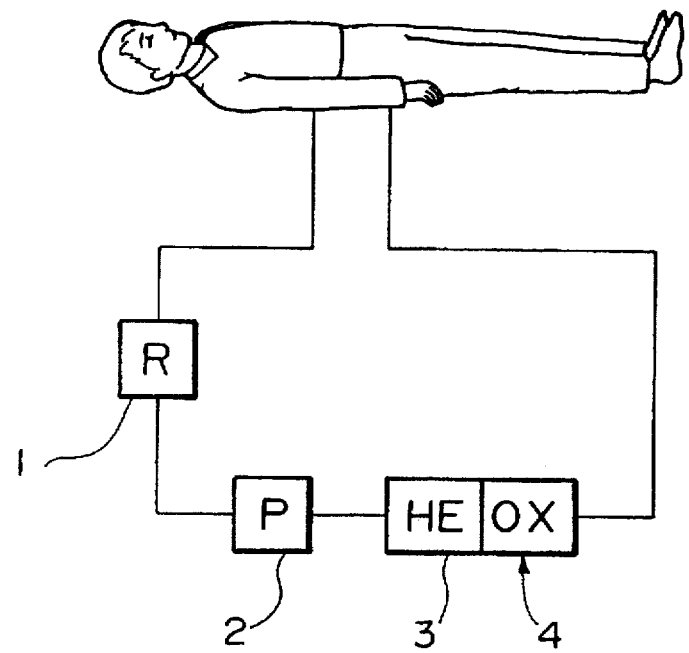
FIG. 3 is circuit diagram of an artificial heart-lung machine provided to explain the composition of a heart-lung machine.
Figure 4:
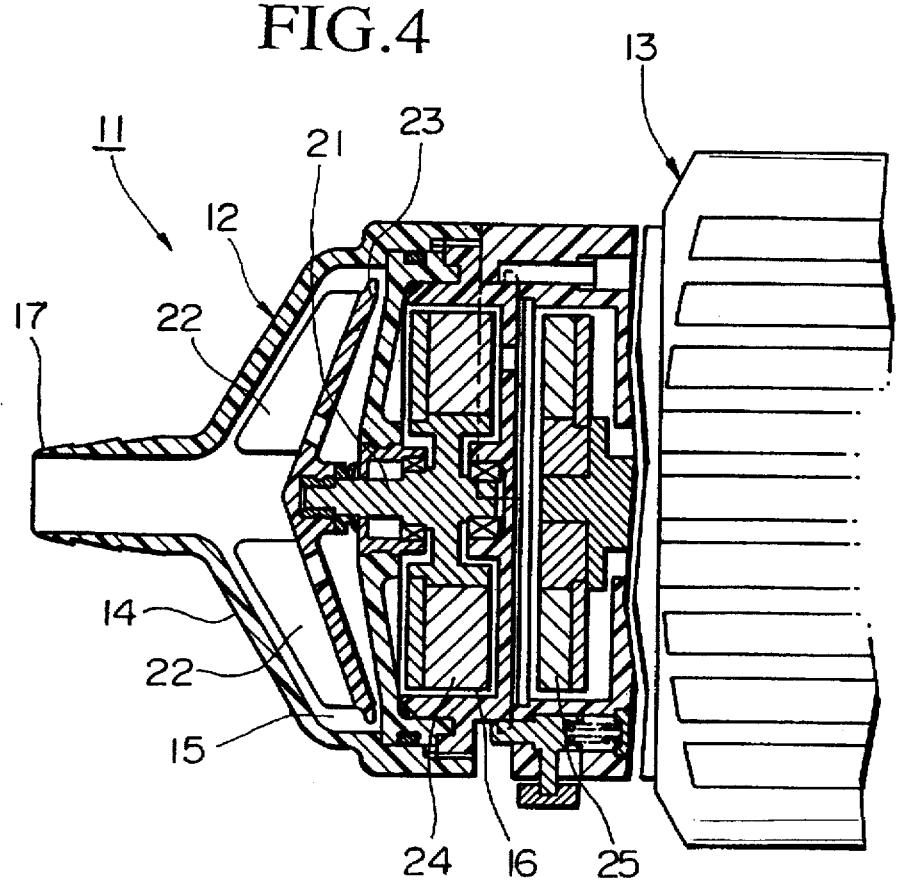
FIG. 4 is a cross-sectional diagram of a centrifugal pump provided to explain the structure and construction of a centrifugal pump.

As shown in FIGS. 1 and 2, in the centrifugal pump 41 of the present embodiment, the centrifugal main body 12 is connected to drive portion 13 as follows.

As shown in FIG. 1, in this centrifugal pump main body 12, blood outlet 18 is directed upward and supported in this state, so that a vertical line X passing through the center point O of centrifugal pump main body 12 is positioned between two straight lines α,β which respectively pass through center point O and a point A and center point O and a point B, points A and B lying on the circumference of centrifugal chamber 15 where its periphery connect with blood outlet 18.

Further, as shown in FIG. 2, in centrifugal pump main body 17, blood inlet 17 is directed upward and supported in this state with a tilt angle δ which is larger with respect to horizontal line Z than the tilt angle γ which is formed between axis Y and the tapered inner peripheral surface of centrifuge chamber 15.

Figure 5:
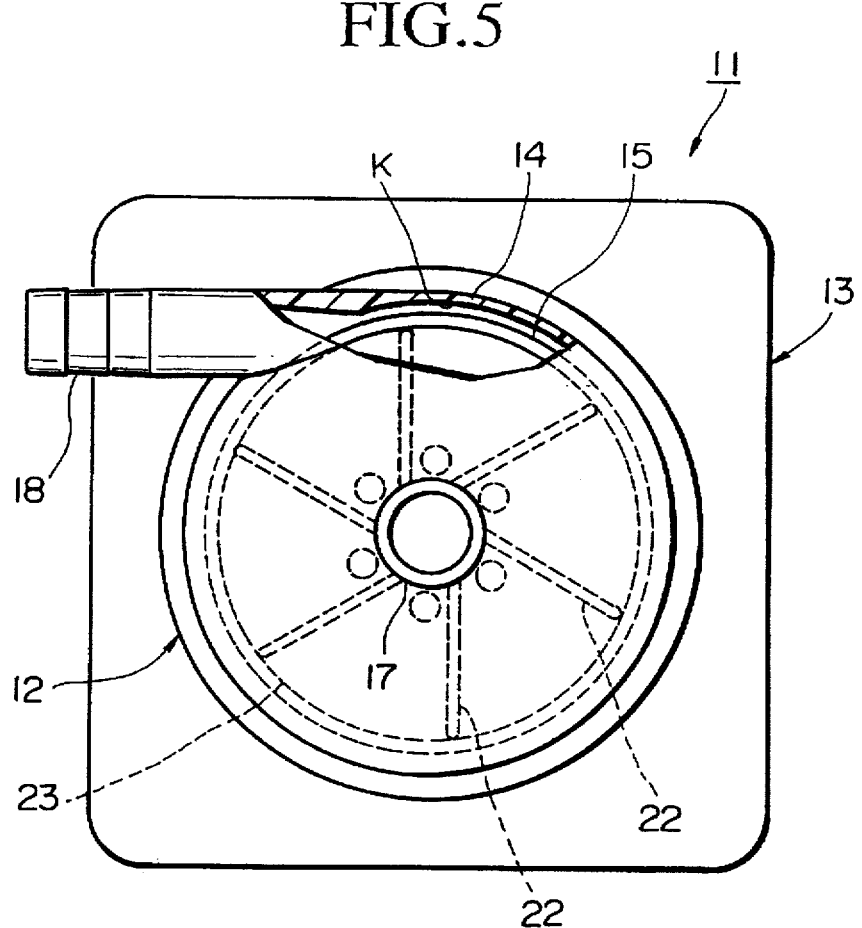
FIG. 5 is a front view of a centrifugal pump provided to explain the structure and construction of centrifugal pump.
Figure 9:
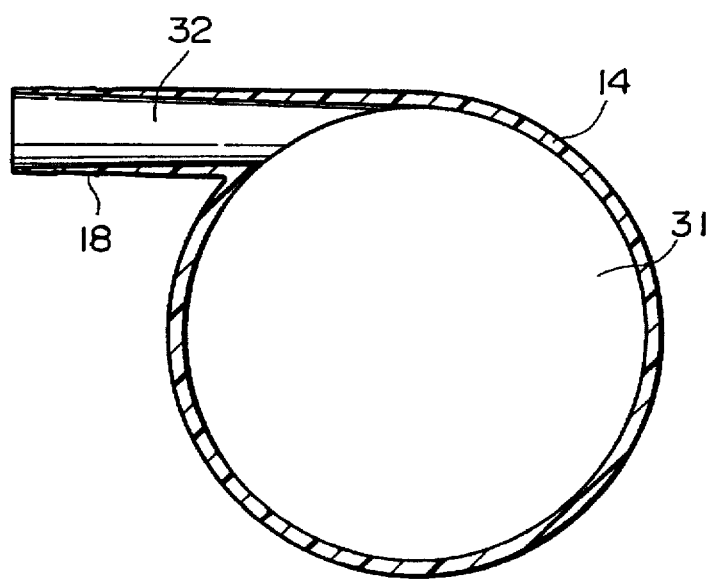
FIG. 9 is a front view of the funnel of the vessel seen in cross-section provided to explain the funnel of the vessel of the centrifugal pump main body.
Figure 6:
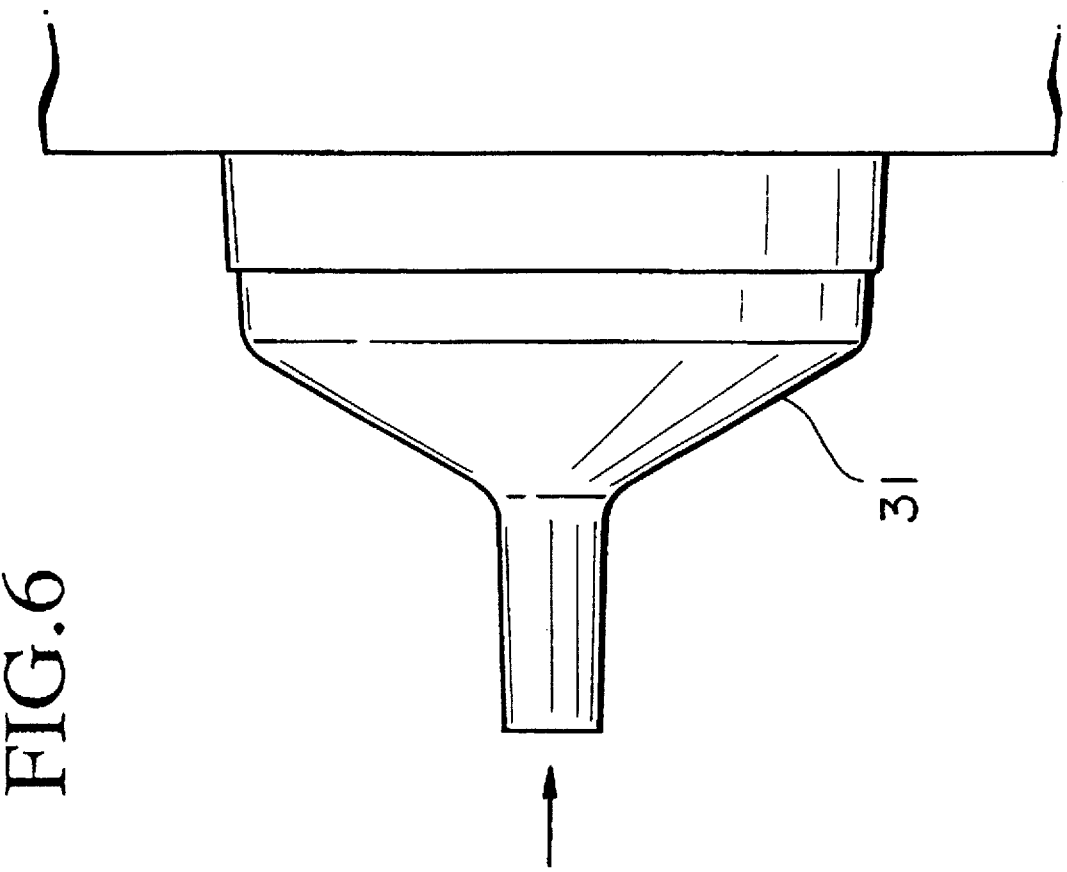
FIG. 6 is a side view of the funnel of the vessel shown in cross-section provided to explain the funnel which composes the vessel of the centrifugal pump main body.
Figure 6:
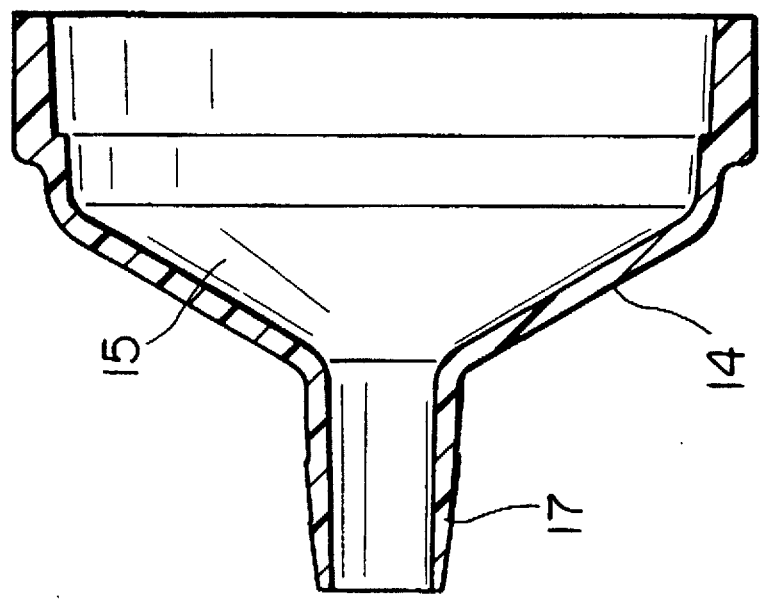
Figure 7:
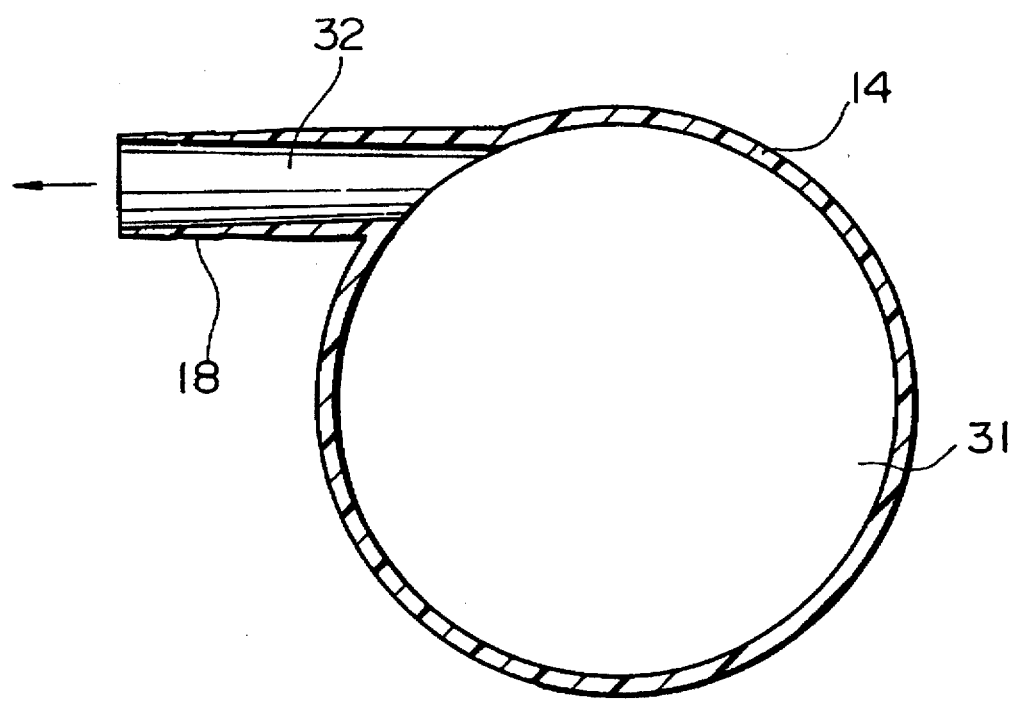
FIG. 7 is a plan view of the funnel of the vessel seen in cross-section provided to explain the funnel which composes the vessel of the centrifugal pump main body.
Figure 8:
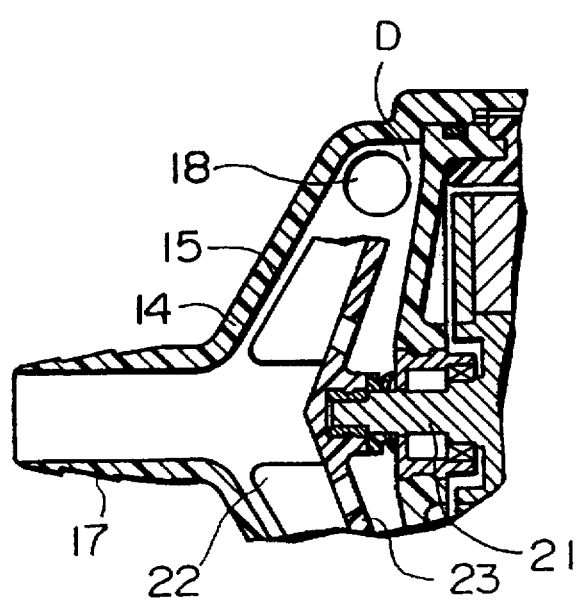
FIG. 8 is a cross-sectional view of a portion of the centrifugal pump main body provided to explain how air bubbles linger inside the centrifuge chamber of the centrifugal pump main body.

In other words, in this centrifugal pump 41, because centrifugal pump main body 12 is supported in a state wherein it is tilted as described above, it is possible to obtain a centrifugal pump with a centrifuge chamber 15 which does not have an area in which air bubbles linger (i.e., an area such as that indicated by D in FIG. 8 and K in FIG. 5), as occurred in the conventional art.

Accordingly, when forcing the blood and liquid filling to flow into the centrifuge chamber 15 from the tube, (not shown in the figures) which is to circulate the blood in the circulation path of the artificial heart-lung machine and which is connected to blood inlet 17 of centrifugal pump main body 12, and then flow out from blood outlet 18 to the tube (not shown in the figures) connected to blood outlet 18, air bubbles do not linger within centrifugal pump main body 12 but are expelled from blood outlet 18 in the blood and liquid filling.

However, air bubbles may become attached and remain to recessed contoured areas such as the vanes 22,22. In these cases, it is necessary to remove the attached air bubbles.

In order to do so, in the present embodiment, centrifugal pump 41 is driven in the following way to carry out the elimination of remaining air bubbles when circulation of the blood and liquid filling is initiated.

(1) The motor of drive portion 13 is operated at low speed (500 to 1500 rpm), rotating at low speed drive magnet 25 of drive portion 13.

In so doing, drive magnet 25 of drive portion 13 is also rotated, rotating magnet 24 of centrifugal pump main body 12. Accompanying this, rotating body 23 rotates.

As a result, an eddy is generated by vanes 22,22 in the blood and liquid filling inside the centrifuge chamber 15, giving rise to a pressure difference in the blood and liquid filling inside centrifuge chamber 15.

In other words, the pressure at the outer peripheral side in centrifuge chamber 15 becomes large, while the pressure around the vicinity of blood inlet 17 becomes small.

Accordingly, the air bubbles which remained inside centrifuge chamber 15 move toward blood inlet 17 which is at low pressure.

Because rotating body 23 is rotating at low speed at this time, the remaining air bubbles within centrifuge chamber 15 do not break up into smaller air bubbles, but move toward blood take-in container 17.

Additionally, it is noted here that the duration of this low speed rotation is of a time length (5 to 30 seconds) sufficient for the remaining air bubbles to move toward blood inlet 17.

(2) Next, by halting the motor of the drive portion 13, the rotation of rotating body 23 is halted.

In so doing, the pressure difference at the centrifuge chamber 15 is eliminated, the air bubbles which moved to blood inlet 17 in process (1) above move toward the upper end of the centrifuge chamber 15 due to buoyant force.

Additionally, it is noted here that the duration during which the motor of drive portion 13 is halted is of a time length (5 to 30 seconds) which is sufficient for the aforementioned air bubbles to move toward the upper end of centrifuge chamber 15.

(3) Then, the motor of drive portion 13 is again rotated to rotate rotating body 23 of centrifugal pump main body 12 at high speed (2500 to 5000 rpm) for a fixed period of time (10 to 120 seconds).

In so doing, as in (1) above, a pressure difference is generated in centrifuge chamber 15. However, because the rotation is carried out at high speed, and the air bubbles which moved to the area around the upper end of centrifuge chamber 15 are flushed out from blood outlet 18 to the tube along with the blood and liquid filling as a result of centrifugal force.

By carrying out operations (1) through (3), the air bubbles which remained in centrifuge chamber 15 can be expelled with ease and surety from blood outlet 18, and centrifuge chamber 15 of centrifugal pump main body 12 can be filled with the blood and liquid filling.

After filling the circulation path with the blood and liquid filling, centrifugal pump 41 is driven at an ordinary number of rotations (1500 to 3000 rpm), carrying out circulation of the blood outside the patient's body.

In this way, by means of the centrifugal pump and air bubble elimination method of the above described embodiment, it is possible to eliminate air bubbles lingering at sites which have a shape conducive to causing this phenomenon and to greatly improve the safety of the artificial heart-lung machine.

Further, it is possible to eliminate with extreme ease and surety the air bubbles which remained in centrifugal pump main body 12 at the time of initiation of circulation of the blood. In other words, the time and labor required for air bubble elimination operations when initiating use of centrifugal pump 41 can be greatly reduced.

Additionally, it is noted here that the above described preferred embodiment of the present invention used the situation where the centrifugal pump 41 is provided in the middle of the circulation path of the artificial heart-lung machine as an illustrative example. However, centrifugal pump 41 is not limited to the path of the artificial heart-lung machine, but may be suitably employed anywhere in the circulation path.

Further, when eliminating air bubbles in centrifuge chamber 15 of centrifugal pump main body 12, the duration during which drive portion 13 is driven, the duration during which driving is halted, the rotating speed and the like are not limited to the preferred embodiments, but may of course be suitably changed in accordance with the size or the like of the centrifugal pump main body 12.

Furthermore, in the above described preferred embodiment, a construction wherein magnet 24 of centrifugal pump main body 12 is rotated by the magnetic force of drive magnet 25 which rotates at the drive portion 13 side was employed as the means for rotating rotating body 23 in centrifugal pump main body 12. However, the means for rotating rotating body 23 inside centrifugal pump main body 12 is not limited to the above described embodiment.

Furthermore, provided that it is a magnetic body which is attracted by the magnetic force of drive magnet 25, the magnet used for magnet 24 of centrifugal pump main body 12 is not particularly restricted.

Industrial Field of Application

As described above, the bubble elimination method in a medical centrifugal pump according to the present invention allows air bubbles remaining in the centrifugal pump main body to be eliminated with extreme ease and surety at the time of initiation of circulation of the blood. Namely, the present invention is appropriately employed to greatly reduce the time and labor of air bubble elimination operations at the time of initiation of use of a centrifugal pump.

What is claimed is:

1. A bubble elimination method in a medical centrifugal pump wherein the centrifugal pump comprises a drive portion and a centrifugal pump main body connected to the drive portion, the centrifugal pump main body being equipped with a vessel wherein there is formed a blood inlet into which the blood and liquid filling flows and a blood outlet from which the blood and liquid filling is sent out, the inner portion of this vessel forming the centrifuge chamber, a shaft which is rotated by the drive portion inside the vessel, a rotating body which is supported by the end of the shaft and rotates inside the centrifuge chamber of the vessel, and a plurality of vanes formed to the rotating body which employ centrifugal force on the blood and liquid filling taken in from the blood inlet by means of the rotation of the rotating body; said method being characterized in that:

a low speed drive process, which is intended to move the remaining air bubbles in the centrifuge chamber toward the blood inlet without breaking the air bubbles into smaller air bubbles, wherein the pressure in the vicinity of the blood inlet is lowered by rotating the rotating body at low speed by means of the drive portion;

a drive halt process, which is intended to move the remaining air bubbles which have been moved toward the blood inlet toward the blood outlet positioned above, wherein the rotation of the rotating body is halted by the drive portion;

a high speed drive process higher than said low speed, which is intended to expel from the blood outlet the remaining air bubbles which have been moved toward the blood outlet, wherein the rotating body is rotated at high speed by the drive portion;

said processes being carried out sequentially after the centrifuge chamber has been filled with blood and liquid filling.

2. A bubble elimination method in a medical centrifugal pump according to claim 1 characterized in that, in the centrifugal pump main body, the blood inlet is formed along the axis of the shaft and the blood outlet is formed to the upper portion of the vessel at the side thereof lying in the tangential direction, the blood outlet of the centrifugal pump being directed upward supported in this state by the drive portion so that a vertical line passing through the center point of the centrifugal pump main body is positioned between two straight lines which respectively pass through the center point and two points lying on the circumference of the centrifuge chamber where its periphery connects with the blood outlet.

3. A bubble elimination method in a medical centrifugal pump according to claim 2 characterized in that the inner peripheral surface of the centrifuge chamber in the centrifugal pump main body forms a tapered surface which progressively widens in the direction moving away from the blood inlet, and the blood inlet is directed upward at an angle which is greater than the angle which is formed between the axis and the inner peripheral surface of the centrifuge chamber supported in this state by the drive portion.

4. A bubble elimination method in a medical centrifugal pump according to claim 1 characterized in that the rotating body of the centrifugal pump main body is rotated at 500 to 1500 rpm during the low speed drive process.

5. A bubble elimination method in a medical centrifugal pump according to claim 1 characterized in that the duration of rotation of the rotating body of the centrifugal pump main body during the low speed drive process is 5 to 30 seconds.

6. A bubble elimination method in a medical centrifugal pump according to claim 1 characterized in that the duration during which the rotating body of the centrifugal pump main body is halted during the drive halt process is 5 to 30 seconds.

7. A bubble elimination method in a medical centrifugal pump according to claim 1 characterized in that the rotating body of the centrifugal pump main body is rotated at 2500 to 5000 rpm during the high speed drive process.

8. A bubble elimination method in a medical centrifugal pump according to claim 1 characterized in that the duration of rotation of the rotating of the centrifugal pump main body during the high speed drive process is 10 to 120 seconds.

9. A bubble elimination method in a medical centrifugal pump according to claim 1 characterized in that a magnetic body is provided to the shaft and a drive magnet which is rotated by a motor is provide to the drive portion, the magnetic body being attracted by the drive magnet and rotated as a result of the rotation of the drive magnet by the motor.

* * * * *

UNITED STATES PATENT AND TRADEMARK OFFICE
CERTIFICATE OF CORRECTION

PATENT NO. : 5,676,526
DATED : October 14, 1997
INVENTOR(S) : Katsuyuki Kuwana et al.

It is certified that error appears in the above-identified patent and that said Letters Patent is hereby corrected as shown below:

On the title page, item:
[73] Assignee: After "Senko Medical Instrument Mfg. Co., Ltd., Tokyo, Japan", please add --and Nikkiso Co., Ltd., Tokyo, Japan--.

Signed and Sealed this

Twenty-fourth Day of March, 1998

Attest:

BRUCE LEHMAN

*Attesting Officer*     *Commissioner of Patents and Trademarks*